United States Patent [19]

Wätjen et al.

[11] Patent Number: 4,999,353

[45] Date of Patent: * Mar. 12, 1991

[54] CHEMICAL PROCESS FOR THE PREPARATION OF IMIDAZO-QUINOXALINES AND INTERMEDIATES FOR USE IN THE PROCESS

[75] Inventors: Frank Wätjen; Holger C. Hansen, both of Vaerlose, Denmark

[73] Assignee: Novo Nordisk A/S, Bagsvaerd, Denmark

[ * ] Notice: The portion of the term of this patent subsequent to Nov. 6, 2007 has been disclaimed.

[21] Appl. No.: 433,668

[22] Filed: Nov. 8, 1989

[30] Foreign Application Priority Data

Nov. 10, 1988 [DK] Denmark ............................ 6262/88

[51] Int. Cl.$^5$ .................. C07D 487/04; C07D 241/44; A61K 31/495; C07B 37/06
[52] U.S. Cl. .................................... 514/250; 544/346; 544/354
[58] Field of Search .......................... 544/346; 514/250

[56] References Cited

U.S. PATENT DOCUMENTS

| | | | |
|---|---|---|---|
| 4,440,929 | 4/1984 | Lee | 544/343 |
| 4,774,245 | 9/1988 | Watjen | 544/343 |
| 4,873,244 | 10/1989 | Watjen | 544/346 |

FOREIGN PATENT DOCUMENTS 320136  6/1989  European Pat. Off. ............ 544/346

OTHER PUBLICATIONS

Watjen I, Chem. Abs. 110, 57685.
Watjen III, Chem. Abs. 109, 110456e (1987).

*Primary Examiner*—Mark Berch
*Attorney, Agent, or Firm*—Gordon W. Hueschen

[57] ABSTRACT

The invention relates to a dealkylation chemical process for preparing imidazoquinoxalines bearing hydrogen substitution in the five position, and to valuable pharm-intermediates of the formula I

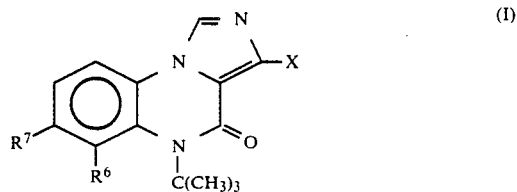

wherein

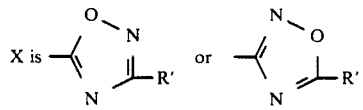

wherein R' is $C_{1-6}$-alkyl, $C_{3-7}$-cycloalkyl, phenyl, thienyl, or $C_{1-3}$-alkoxymethyl
  and wherein $R^6$ and $R^7$ independently are hydrogen, halogen or $CF_3$, used in that process. The intermediates also have anticonvulsant and anxiolytic properties.

6 Claims, No Drawings

CHEMICAL PROCESS FOR THE PREPARATION OF IMIDAZO-QUINOXALINES AND INTERMEDIATES FOR USE IN THE PROCESS

This invention relates to a novel chemical process for preparing imidazoquinoxalines bearing hydrogen substitution in the five position, and to novel intermediates used in that process. The novel intermediates also have valuable pharmacological properties.

Danish patent application 4996/86 (corresponding to U.S. patent application Ser. No. 912,776, filed Sept. 26, 1986 and issued as U.S. Pat. No. 4,774,245 on Sept. 27, 1988) discloses quinoxaline compounds having the general formula A

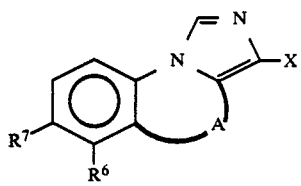

(A)

wherein

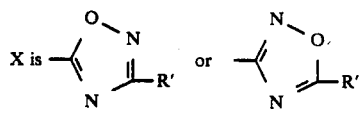

wherein R' is $C_{1-6}$-alkyl, $C_{3-7}$-cycloalkyl, phenyl, thienyl, or $C_{1-3}$-alkoxymethyl $R^6$ and $R^7$ each is hydrogen or halogen, and

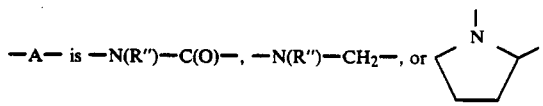

wherein R" is hydrogen, $C_{3-7}$-cycloalkyl or $C_{1-6}$-alkyl.

The above compounds are disclosed as having pharmacological properties that make them useful as for example anticonvulsants and anxiolytics. The compounds are according to Danish patent application 4996/86 corresponding to U.S. patent application Ser. No. 912,776, filed Sept. 26, 1986 and issued as U.S. Pat. No. 4,774,245 on Sept. 27, 1988) prepared by:

(a) reacting a compound of formula II

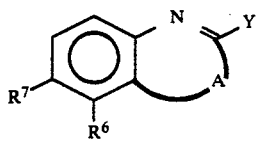

(II)

wherein —A—, $R^6$ and $R^7$ have the meanings set forth above and wherein Y is a leaving group, with a compound having the formula III

 (III)

wherein X has the meaning set forth above, (b) reacting a reactive derivative of a compound having the general formula IV

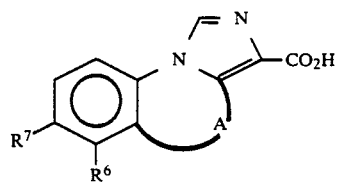

(IV)

wherein —A—, $R^6$ and $R^7$ have the meanings set forth above, with a compound having the general formula V

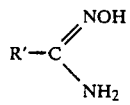

(V)

wherein R' has the meaning set forth above, to form a compound of the general formula I, wherein X is

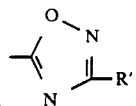

wherein R' has the meaning set forth above, (c) reacting a compound having the general formula VI

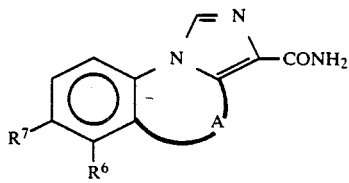

(VI)

wherein —A—, $R^6$ and $R^7$ have the meanings set forth above, with a compound having the general formula VII

 (VII)

wherein R' has the meaning set forth above to form a compound having the general formula VIII

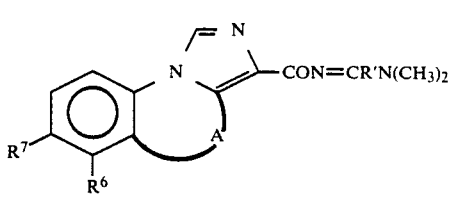

(VIII)

wherein R', —A—, $R^6$ and $R^7$ have the meanings set forth above, and reacting the compound thus formed with $NH_2OH$ or another aminating agent to form a compound having the general formula I, wherein X is

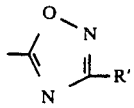

wherein R' has the meaning defined above, or (d) reacting a compound having the general formula IX

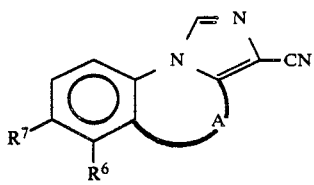

wherein —A—, $R^6$ and $r^7$ have the meanings set forth above, with $NH_2OH$ to form a compound having the general formula X

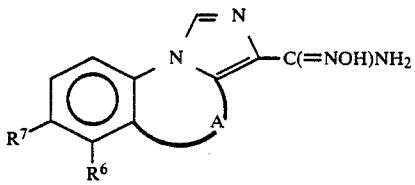

wherein —A—, $R^6$ and $R^7$ have the meanings set forth above, and reacting the compound thus formed with R'—COCl, wherein R' has the meaning set forth above, to form a compound of formula I, wherein X is

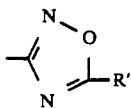

wherein R' has the meaning set forth above.

We have now discovered a new process for the preparation of above compounds having the formula A, as well as for novel compounds.

Accordingly, the present invention provides a process for preparing novel intermediates for above compounds of formula A, as well as novel compounds also having anticonvulsant and anxiolytic properties.

The novel process of the present invention comprises the step of dealkylating a compound having the general formula I

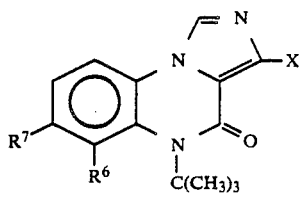

wherein

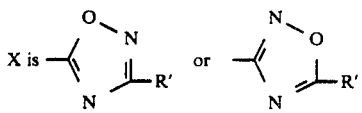

wherein R' is $C_{1-6}$-alkyl, $C_{3-7}$-cycloalkyl, phenyl, thienyl, or $C_{1-3}$-alkoxymethyl and wherein $R^6$ and $R^7$ independently are hydrogen, halogen or $CF_3$, to form a compound of the general formula B

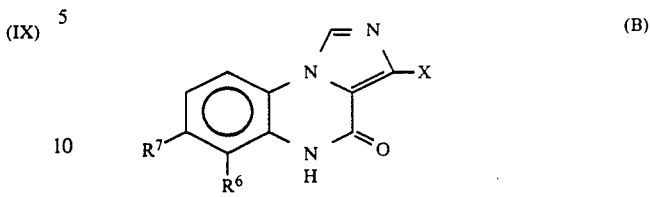

wherein X, $R^6$ and $R^7$ have the meanings defined above.

The compounds of formula B are useful in the preparation of compounds of formula A as well as for the preparation of other imidazoquinoxalines.

The following examples illustrate the novel process of the present invention, the novel intermediates of the present invention and the utility of the novel intermediates of the present invention.

EXAMPLE 1

N-tert-butyl-N-ethoxalyl-2-nitroaniline

To a stirred solution of 2-nitro-N-tert-butylaniline (37 g) and triethylamine (35 ml) in tetrahydrofuran (400 ml) was added dropwise a solution of ethoxalyl chloride (25 ml) in tetrahydrofuran (50 ml). The mixture was then brought to reflux temperature for 8 h. The solvent was removed by evaporation, and the residue was partitioned between ether (300 ml) and water (500 ml). The organic phase was washed twice with water, dried over $Na_2SO_4$ and evaporated. This left the title compound as light yellow crystals, m.p. 73°–74° C.

N-tert-butyl-N-ethoxalyl-o-phenylenediamine

A solution of N-tert-butyl-N-ethoxalyl-2-nitroaniline (45 g) in absolute ethanol (500 ml) was hydrogenated at standard conditions (1 atm.) using 5% Pd/C (5 g) as catalyst. The catalyst was filtered off and the solvent was removed in vacuo. This left an oil, which crystallized upon standing, m.p. 64°–65° C.

(1-tert-butyl-1,2,3,4-tetrahydro-2,3-dioxo-quinoxaline

The neat crystals of N-tert-butyl-N-ethoxalyl-o-phenylene diamine (88 g) were heated to 100° C. for 4 h. The crude product hereby deposited from the melt as crystals. After cooling to ambient temperature the solid taken in ether and the product was filtered off as white crystals, m.p. >300° C.

5-tert-butyl-3-(5-cyclopropyl-1,2,4-oxadiazol-3-yl)-4,5-dihydro-4-oxo-imidazo[1,5-a]quinoxaline To a stirred solution of 1-tert-butyl-1,2,3,4-tetrahydro-2,3-dioxo-quinoxaline (0.5 g, 2.3 mmol) in dry dimethylformamide (DMF) (30 ml) was added potassium t-butylate (0.34 g, 3 mmol). After additional stirring for 15 min. diethyl chlorophosphate was added (0.43 ml, 3 mmol). Stirring was continued at ambient temperature for further 20 min., whereafter the solution was cooled to −30° C. 5-cyclopropyl-3-isocyanomethyl-1,2,4-oxadiazole (0.5 g, 3.5 mmol) was now added followed by the addition of a solution of potassium t-butylate (0.5 g, 3.5 mmol) in DMF (15 ml). The mixture was now allowed to attain to room temperature (45 min.) before acetic acid (1 ml) was added. After removal of the solvent in vacuo the residue was partitioned between water: ether (50 ml, 20 ml). This treatment afforded precipitation of the crude title compound as pale crystals, which could be purified by recrystallization from 2-propanol, m.p. 154°-155° C.

In a similar manner the following compound was prepared:

Ethyl 5-tert-butyl-4,5-dihydro-4-oxo-imidazo[1,5-a]quinoxaline-3-carboxylate, m.p. 289°-290° C. by reaction between ethyl isocyanoacetate and 1-tert-butyl-1,2,3,4-tetrahydro-2,3-dioxoquinoxaline 5-tert-butyl-3-(3-cyclopropyl-1,2,4-oxadiazol-5-yl)-4,5-dihydro-4-oxo-imidazo[1,5-a]quinoxaline Ethyl 5-tert-butyl-4,5-dihydro-4-oxo-imidazo[1,5-a]quinoxaline-3-carboxylate (0.5 g), cyclopropancarboxamidoxime and 5 g crushed mol. sieves (4 Å) were added to absolute dry ethanol (30 ml) wherein sodium (40 mg) prevously had been dissolved. The stirred mixture was refluxed for 1.5 h, then cooled to room temperature, and filtered through a pad of celite. The filtrate was evaporated in vacuo to ca. 5 ml and water (25 ml) was added. The precipitated product was filtered off and purified by recrystallization from 2-propanol, m.p. 182°-184° C.

3-(5-cyclopropyl-1,2,4-oxadiazol-3-yl)-4,5-dihydro-4-oxoididazo[1,5-a]quinoxaline A stirred solution of 5-tert-butyl-3-(5-cyclopropyl-1,2,4-oxadiazol-3-yl)-4,5-dihydro-4-oxo-imidazo[1,5-a]quinoxaline (7.9 g) in a mixture of ethanol (75 ml) and aqueous HCl (4N, 30 ml) was refluxed for 10 min, whereby the product precipitated as crystals.

The crystals were removed by filtration and were purified by recrystalllization from methanol, m.p. 308°-310° C.

In a similar manner was prepared:

3-(3-cyclopropyl-1,2,4-oxadiazol-5-yl)-4,5-dihydro-4-oxoidazo[1,5-a]quinoxaline, m.p. >300° C. from 5-tert-butyl-3-(3-cyclopropyl-1,2 4-oxadiazol-5-yl)-4,5-dihydro-4-oxo-imidazo[1,5-a]quinoxaline

EXAMPLE 2

3-(5-cyclopropyl-1,2,4-oxadiazol-3-yl)-5-ethoxycarbonylmethyl-4,5-dihydro-4-oxo-imidazo[1,5-a]quinoxaline To a stirred solution of 3-(5-cyclopropyl-1,2,4-oxadiazol-3-yl)-4,5-dihydro-4-oxo-imidazo[1,5-a]quinoxaline (200 mg) in DMF (10 ml) was added sodium hydride (50 mg) and after 10 min ethyl monochloroacetate (1 ml). The mixture was stirred further for 2 h, whereafter the solvent was removed by evaporation in vacuo. The residue was partitioned between water (25 ml) and ether (20 ml), and the crystalline product was filtered off. M.p. 245°-246° C.

With 3-(5-cyclopropyl-1,2,4-oxadiazol-3-yl)-4,5-dihydro-4-oxo-imidazo[1,5-a]quinoxaline and appropriate halides as starting materials and DMF as solvent the following compounds were prepared:

3-(5-cyclopropyl-1,2,4-oxadiazol-3-yl)-4,5-dihydro-5-(3,3-dimethylallyl)-4-oxo-imidazo[1,5-a]quinoxaline, m.p. 133°-134° C. by alkylation with 3,3-dimethyialiyl bromide.

5-allyl-3-(5-cyclopropyl-1,2,4-oxadiazol-3-yl)-4,5-dihydro-4-oxo-imidazo[1,5-a]quinoxaline, m.p. 188°-189° C. by alkylation with allyl bromide.

3-(5-cyclopropyl-1,2,4-oxadiazol-3-yl)-4,5-dihydro-4-oxo-5-phenacyl-imidazo[1,5-a]quinoxaline, m.p. 258°-259° C. by alkylation with phenacyl bromide 5-acetonyl-3-(5-cyclopropyl-1,2,4-oxadiazol-3-yl)-4,5-dihydro-4-oxo-imidazo[1,5-a]quinoxaline, m.p. 280°-282° C. by alkylation with chloroacetone. Recrystallization from methanol.

3-(5-cyclopropyl-1,2,4-oxadiazol-3-yl)-5-(2-fluorobenzyl)-4,5-dihydro-4-oxo-imidazo[1,5-a]quinoxaline, m.p. 229°-230° C. by benzylation with 2-fluorobenzyl chloride. Recrystallization from toluene.

3-(5-cyclopropyl-1,2,4-oxadiazol-3-yl)-4,5-dihydro-5-(2-methylbenzyl)-4-oxo-imidazo[1,5-a]quinoxaline, m.p. 235°-237° C. by benzylation with 2-methyl-benzyl chloride. Recrystallization from methanol.

5-(2-bromobenzyl)-3-(5-cyclopropyl-1,2,4-oxadiazol-3-yl)-4,5-dihydro-4-oxo-imidazo[1,5-a]quinoxaline, m.p. 236-237 by benzylation with 2-bromobenzyl bromide 3-(5-cyclopropyl-1,2,4-oxadiazol-3-yl)-4,5-dihydro-5-(3-methoxybenzyl)-4-oxo-imidazo[1,5-a]quinoxaline, m.p. 188°-190° C. by benzylation with m-methoxybenzyl chloride, m.p. 188°-190° C. Recrystallization from toluene.

3-(5-cyclopropyl-1,2,4-oxadiazol-3-yl)-5-(2-ethoxyethyl-4,5-dihydro-4-oxo-imidazo[1,5-a]quinoxaline, m.p. 161°-162° C. by alkylation with 2-bromoethylethylether. Recrystallization from ethanol.

3-(5-cyclopropyl-1,2,4-oxadiazol-3-yl)-4,5-dihydro-4-oxo-5-(4-phthalimidobenzyl)-imidazo[1,5-a]quinoxaline, m.p. 280°-282° C. (from dichloromethane-acetone, 4:1) by benzylation with 4-(phthalimido)benzyl chloride.

What is claimed is:

1. A compound having the formula I

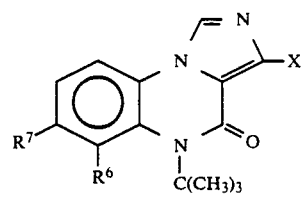

(I)

wherein

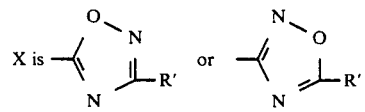

wherein R' is $C_{1-6}$-alkyl, $C_{3-7}$-cycloalkyl, phenyl, thienyl, or $C_{1-3}$-alkoxymethyl and wherein $R^6$ and $R^7$ independently are hydrogen, halogen or $CF_3$.

2. A pharmaceutical composition comprising an effective anticonvulsant or anxiolytic amount of a compound of claim 1 and a pharmaceutically-acceptable carrier or diluent.

3. A compound according to claim 1, which is 3-(3-cyclopropyl-1,2,4-oxadiazol-5-yl)-4,5-dihydro-4-oxo-5-tertbutylimidazo-(1,5-a)quinoxaline.

4. A method of treating a patient in need of anticonvulsant or anxiolytic therapy comprising the step of administering to the said patient an effective anxiolytic or anticonvulsant amount of a compound of claim 1.

5. A method of treating a patient in need of anticonvulsant or anxiolytic therapy comprising the step of administering to the said patient an effective anxiolytic or anticonvulsant amount of a compound of claim 3.

6. A pharmaceutical composition comprising an effective anticonvulsant or anxiolytic amount of a compound of claim 3 and a pharmaceutically-acceptable carrier or diluent.

* * * * *

UNITED STATES PATENT AND TRADEMARK OFFICE
CERTIFICATE OF CORRECTION

PATENT NO. : 4,999,353

DATED : Mar. 12, 1991

INVENTOR(S) : Frank Watjen, Holger C. Hansen

It is certified that error appears in the above-identified patent and that said Letters Patent is hereby corrected as shown below:

Column 1, approximately line 40; 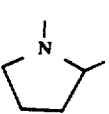 should read -- 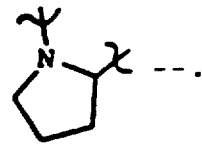 --.

Column 1, line 48; "4996/86 corresponding" should read
   -- 4996/86 (corresponding --.
Column 3, line 14; "r7" should read -- R --.
Column 4, line 49; insert -- was -- before "taken".
Column 4, line 49; insert -- up -- after "taken".
Column 5, line 25; "oxoididazo" should read -- oxoimidazo --.
Column 5, approximately line 36; "oxoidazo" should read
   -- oxoimidazo --.
Column 5, line 37; "1,2  4" should read -- 1,2,4 --.
Column 5, line 59; "alkyiation" should read -- alkylation --.
Column 5, line 59; "dimethyiaiiyl" should read --dimethylallyl --.

Signed and Sealed this

Fifteenth Day of September, 1992

*Attest:*

DOUGLAS B. COMER

*Attesting Officer*  *Acting Commissioner of Patents and Trademarks*